United States Patent [19]

Dougherty et al.

[11] Patent Number: 5,721,009
[45] Date of Patent: Feb. 24, 1998

[54] CONTROLLED CARBON CONTENT MOD PRECURSOR MATERIALS USING ORGANIC ACID ANHYDRIDE

[75] Inventors: Thomas K. Dougherty, Playa Del Rey; O. Glenn Ramer, Los Angeles, both of Calif.

[73] Assignee: HE Holdings, Inc., Los Angeles, Calif.

[21] Appl. No.: 669,122

[22] Filed: Jun. 24, 1996

[51] Int. Cl.$^6$ .................................................. B05D 3/02
[52] U.S. Cl. ......................... 427/126.6; 427/226; 427/240
[58] Field of Search ............................. 556/28, 30, 42, 556/51, 54, 64, 81, 118; 427/126.3, 126.6, 226, 240

[56] References Cited

U.S. PATENT DOCUMENTS

| 4,963,390 | 10/1990 | Lipeles et al. | 427/110 |
|---|---|---|---|
| 5,423,285 | 6/1995 | Paz de Araujo et al. | 117/90 |
| 5,434,102 | 7/1995 | Watanabe et al. | 437/130 |
| 5,439,845 | 8/1995 | Watanabe et al. | 437/130 |
| 5,468,679 | 11/1995 | Paz de Araujo et al. | 437/110 |
| 5,514,822 | 5/1996 | Scott et al. | 556/28 |
| 5,559,260 | 9/1996 | Scott et al. | 556/28 |
| 5,614,252 | 3/1997 | McMillan et al. | 427/99 |

FOREIGN PATENT DOCUMENTS

| 9312542 | 6/1993 | WIPO. |
|---|---|---|
| WO 93/12538 | 6/1993 | WIPO. |

OTHER PUBLICATIONS

G.M. Vest et al, "Synthesis of Metallo–Organic Compounds For MOD Powders and Films", *Mat. Res. Soc. Symp. Proc.*, vol. 60, pp. 35–42 (1986).

R.W. Schwartz et al, "Solution Chemistry Effects in Pb(Zr, Ti) O3 Thin Film Processing", *Integrated Ferroelectrics*, 1992, vol. 2, pp. 243–254 (1992).

San-Yuan Chen et al, "Cracking during Pyrolysis of Oxide Thin Films—Phenomenology, Mechanisms, and Mechanics", *Journal of American Ceramic Society*, vol. 78, No. 11, pp. 2929–2939 (Nov. 1995).

T. Kawahara et al, "Influence of Ti Sources on Properties of (Ba,Sr)TiO$_3$ Films Prepared by Liquid Source CVD", *Mat. Res. Soc. Symp. Proc.*, vol. 361, pp. 361–366 (1995).

C.A–Paz de Araujo*† et al, "Fatigue–free ferroelectric capacitors with platinum electrodes", *Nature*, vol. 374, pp. 627–629 (Apr. 1995).

*Primary Examiner*—Erma Cameron
*Attorney, Agent, or Firm*—M. E. Lachman; M. W. Sales; W. K. Denson-Low

[57] ABSTRACT

Metal organic acid salt solutions for use as precursor materials for forming layered ferroelectric thin films are synthesized using an organic acid anhydride as the exchange reagent. The reaction is much faster than previous techniques, allows exact control of exchange with control of hydrolysis product, and may be used to control the solvent of the final solution. The reaction creates no water, and can be used to exactly control the extent of reaction of all metals. By using less than or equal to a stoichiometric amount of anhydride and then further reacting the remaining alkoxides, lower carbon content solutions with less decomposable organic can be formed. As such, the present invention discloses a much improved and faster synthesis technique giving improved solutions and corresponding thin film metal oxide compositions with improved and consistent electrical performance.

22 Claims, 1 Drawing Sheet

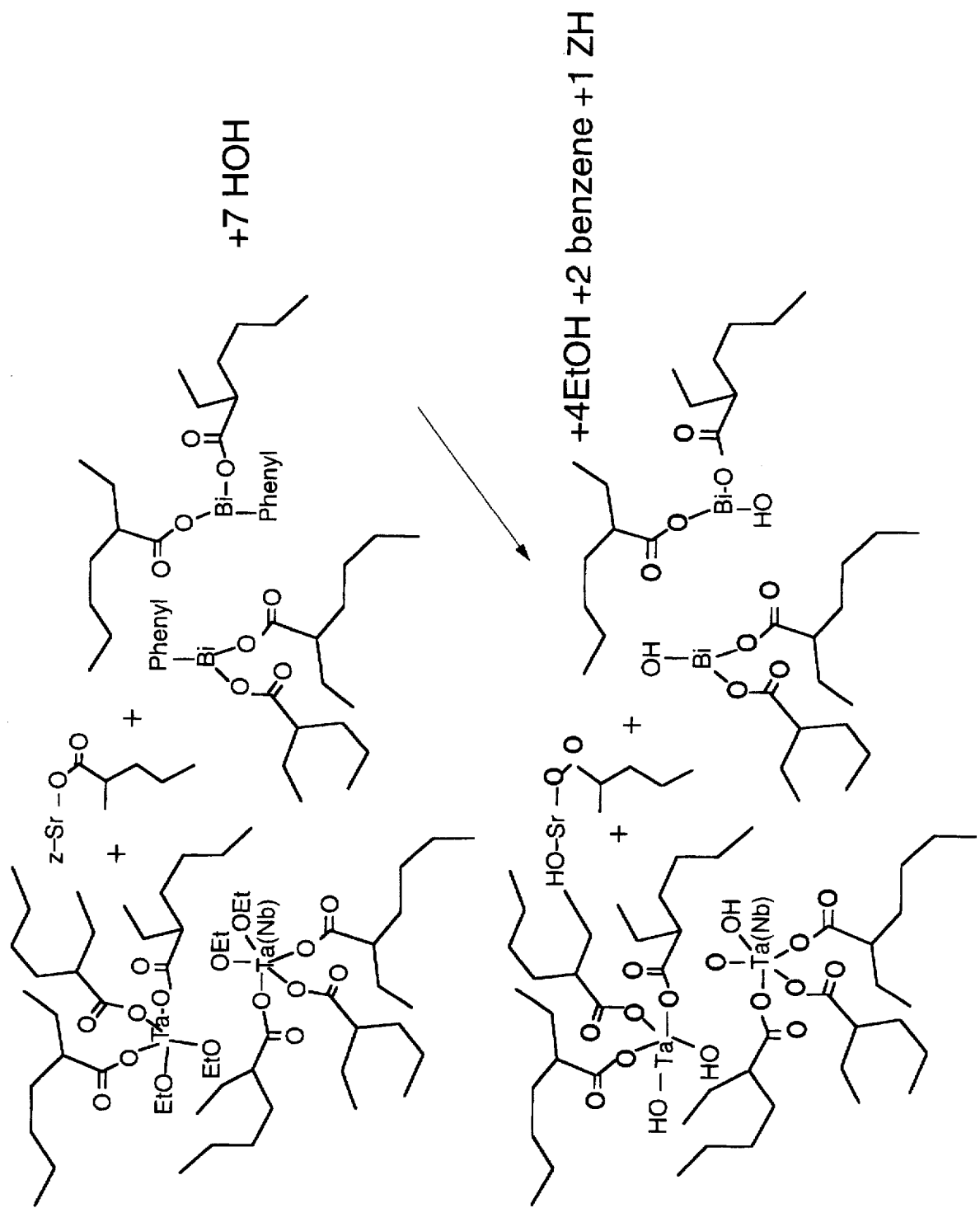

CONTROLLED CARBON CONTENT MOD PRECURSOR MATERIALS USING ORGANIC ACID ANHYDRIDE

This invention was made with United States Government support under Contract No. N00030-95-C-0012 awarded by the Department of the Navy. The U.S. Government has certain rights in this invention.

BACKGROUND OF THE INVENTION

1. Field of the Invention

The present invention relates to an improved process for fabrication of metal oxide materials and devices, and other ceramic thin films via the metalo-organic decomposition method.

2. Description of Related Art

A new class of layered ferroelectric materials having a layered perovskite structure has begun finding use as thin layered ferroelectric films in radiation-hard, non-volatile microelectronic memories, high dielectric constant capacitors, energy storage devices, and the like. These layered materials comprise complex oxides of metals such as strontium, calcium, barium, bismuth, cadmium, lead, titanium, tantalum, hafnium, tungsten, niobium, zirconium, scandium, yttrium, lanthanum, antimony, chromium, and thallium that spontaneously form layered crystalline lattices that include alternating layers of distinctly different sublattices, such as ferroelectric and non-ferroelectric sublattices. Generally, each layered material will include two or more of the above metals. For example, strontium, bismuth, tantalum and niobium form the layered material strontium bismuth tantalum niobate, $SrBi_2Ta_{2-x}Nb_xO_9$ (SBTNO).

In addition to having good values of the ferroelectric parameters, it is also important that the physical quality of the ferroelectric films be suitable for use in manufacturing processes. For example, the film should have a relatively uniform grain size, which results in better thin film quality, i.e., films free of cracks and other defects. The film grain size should also be small compared to the thickness of the film; otherwise, the roughness of the film can be comparable to the thickness and other dimensions of the device components, which makes it difficult or impossible to fabricate devices within tolerances, with concomittant short circuits and other electrical breakdowns. Further, it is important that the fabrication processes be ones that can be performed relatively rapidly, since long processes are more expensive in terms of the use of facilities and personnel.

A variety of techniques has been disclosed for fabricating such layered ferroelectric materials. For example, PCT publication WO 93/12538, entitled "Process for Fabricating Superlattice Materials", by C. A. Paz de Araujo et al, discloses applying a pre-cursor comprising a metal carboxylate, e.g., metal 2-ethylhexanoate, in a xylene solvent to an integrated circuit wafer; see also U.S. Pat. No. 5,434,102, issued to H. Watanabe et al. The wafer is baked to dry the precursor and annealed to form a layered supefiattice material on the wafer.

The foregoing technique employs metallo-organic decomposition (MOD) to form the layered ferroelectric materials; see also G. M Vest et al, "Synthesis of Metallo-Organic Compounds for MOD Powders and Films", *Materials Research Society Symposium Proceedings*, Vol. 60, pp. 35–42 (1986) for another reference describing MOD techniques. Problems with MOD chemistry are described by R. W. Schwartz et al, "Solution Chemistry Effects in Pb(Zr, Ti)O₃ Thin Film Processing", *Integrated Ferroelectrics*, Vol. 2, pp. 243–254 (1992). This reference describes sol-gel, MOD, and hybrid deposition techniques, based on the use of metallo-organic precursors.

In previous work by the present inventor and others, organic metal acid salts are formed via exchange of metal alkoxides with the corresponding acid. This reaction may take several days or longer and allows the contact of acid with alcohol. Those skilled in the art will readily appreciate that such contact may cause water formation, which may hydrolyze the starting materials, intermediates, or products, thereby creating precipitates and oligomers that are difficult to filter, that can upset the stoichiometry, and that may decompose during heat treatment in an uncontrolled manner.

It will be obvious to those skilled in the art that the manufacture of metal organic acid salts from metal alkoxides by acid exchange with an organic acid (for example, the reaction of 2-ethylhexanoic acid with tantalum ethoxide) may be very difficult to exactly control due to the formation of water and esters. The esters consume available acid for the acid-alcohol interchange, and the water formed may hydrolyze the unreacted metal alkoxide. It is noted that other investigators using the above-mentioned MOD and sol-gel process for production of electronic thin films have shown that these variables must be kept under careful control to eliminate cracking and other problems; see, e.g., S.-Y. Chen et al, "Cracking during pyrolysis of oxide thin films—phenomenology, mechanisms, and mechanics", *Journal of the American Chemical Society*, Vol. 78, pp. 2929–2939 (1995) and T. Kawahara et al, "Influence of Ti Sources on Properties of (Ba, Sr)TiO₃ Films Prepared by Liquid Source CVD", *Materials Research Society Symposium Proceedings*, Vol. 361, pp. 361–366 (1995), for the case of BST thin films. The present inventor has also found this to be the case, as will be discussed below, for the SBTNO thin films.

Thus, there is a need for a process that requires less time, avoids the formation of esters and water, and can be used to exactly control the chemical nature of the desired product.

SUMMARY OF THE INVENTION

In accordance with the present invention, metal organic acid salt solutions are synthesized using an organic acid anhydride as the exchange reagent. The reaction is much faster than previous techniques, allows exact control of exchange with control of hydrolysis product, and may be used to control the solvent of the final solution. The reaction creates no water, and can be used to exactly control the extent of reaction of all metals. By using less than or equal to a stoichiometric amount of anhydride and then further reacting the remaining alkoxides, lower carbon content solutions with less decomposable organic can be formed. As such, the present invention discloses a much improved and faster synthesis technique giving improved solutions and corresponding thin film metal oxide compositions with improved electrical performance.

The process of the present invention comprises:

(1) providing an organic acid anhydride;

(2) forming a first reaction mixture of less than or equal to a stoichiometric amount of the organic acid anhydride with at least one metal alkoxide;

(3) removing by-products of the foregoing reactions to leave a product; and (4) adding at least one solvent to the product to provide a liquid which comprises a mixture of mixed metal organic acid soluble materials having a controlled carbon content and which forms quality crack-free films when deposited on a substrate.

In the present invention, if the final product is intended to be a bismuth-based compound, then prior to Step (1), less than or equal to a stoichiometric amount of an acid is reacted with a bismuth-containing organic compound to form a first reaction mixture and that mixture is then reacted with the metal alkoxide(s) formed in Step (2). Advantageously, the acid is the free acid form of the acid anhydride employed in Step (1).

The final reaction product resulting from Step (4) may be employed as a spin-on-coating useful in making improved metal oxide thin film electronic devices.

BRIEF DESCRIPTION OF THE DRAWINGS

The sole FIGURE is a representation of the mixed metal alkoxide organic acid materials formed in accordance with the process of the present invention.

DESCRIPTION OF THE PREFERRED EMBODIMENTS

The present invention is directed to a fast, completely controlled exchange which never allows acid and alcohol in direct contact, creates no water, and can be used to exactly control the extent of reaction of all metals. In this connection, it is noted that the prior art processes failed to control reaction of the metal alkoxides.

By using less than or equal to a stoichiometric amount of anhydride, then further reacting the remaining alkoxides, lower carbon content solutions with less decomposable organic can be formed. As such, the present invention discloses a much improved and faster synthesis technique giving improved solutions and corresponding thin film metal oxide compositions with improved electrical performance.

The process of the present invention comprises:

(1) providing a first organic acid anhydride, e.g., 2-ethylhexanoic acid anhydride;

(2) forming a first reaction mixture of less than or equal to a stoichiometric amount of the first organic acid anhydride with at least one metal alkoxide, e.g., a mixture of niobium, tantalum, and strontium alkoxides;

(3) removing the by-products of the foregoing reactions to leave a product, such by-products including, for example, the alkoxide esters of 2-ethylhexanoic acid and any alcohols, employing, for example, vacuum distillation; and (4) adding at least one solvent to the product to provide a liquid which comprises a mixture of mixed metal organic acid soluble materials having a controlled carbon content and which forms quality crack-free films when deposited on a substrate.

Optionally, water or a hydroxy-containing compound, such as a difunctional acid or alcohol, may be added to the product resulting from Step (3), followed by partial or complete hydrolyzation (or reacting the difunctional acid or alcohol) to form the mixture of mixed metal organic soluble materials. The solvent(s) added in Step (4) render the mixture suitable for the formation of metal oxide thin film electronic devices.

In the present invention, if the final product is intended to be a bismuth-based compound, then prior to Step (1), less than or equal to a stoichiometric amount of an acid is reacted with a bismuth-containing organic compound, e.g., triphenyl bismuth, to form a first reaction mixture and that mixture is then reacted with the metal alkoxide(s) formed in Step (2). The by-products subsequently removed will then also include benzene. Advantageously, the acid is the free acid form of the acid anhydride employed in Step (1).

The final reaction product may be used as is or further modified via solvent exchange followed by condensation to give a mixed metal soluble material suitable for use as a spin-on-coating useful in making improved metal oxide thin film electronic devices.

Each step is now described in detail with reference to a specific example, which is directed to the preparation of SBTNO. However, alternative embodiments are also described in each step. Further, it will be appreciated that the process is not limited to the described example, but is useful for the preparation of the entire family of compositions used in fabricating ceramic oxide thin films. Following the description of the process of the invention, the electrical properties of the improved device are described.

1. Synthesis of 2-ethylhexanoic Acid Anhydride

To a mechanical stirred solution of dicyclohexyl carbodiimide (150 g, 0.727 mol) (II) in 1 liter of hexane/toluene was added 2-ethylhexanoic acid (209 g, 1.44 mol) (I). The structure of 2-ethylhexanoic acid (EHA, I) is shown below; however, in the reaction sequence, it is shown in its skeletal form.

The reaction was stirred overnight. Copious amounts of a white solid (the by-product dicyclohexyl urea (III)) were formed. The white solid was filtered, the flitrate concentrated on a rotary evaporator and then vacuum distilled to give a product (120 g, b.p. 106°–110° C. at 0.5 torr) whose analytical ($C^{13}$ and $H^1$ NMR) were consistent with the desired product 2-ethylhexanoic acid anhydride (III): $C^{13}$ NMR ($CDCl_3$): 171.6, 48.0, 30.8, 29.1, 24.6, 22.4, 13.6, 11.3.

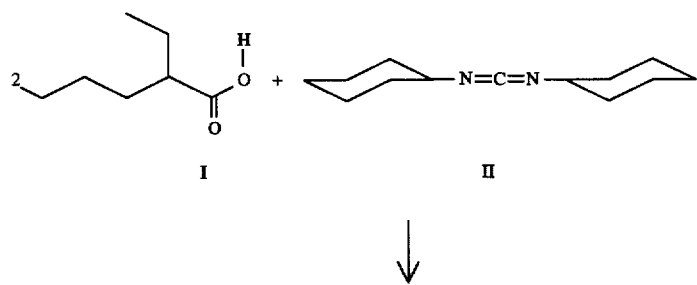

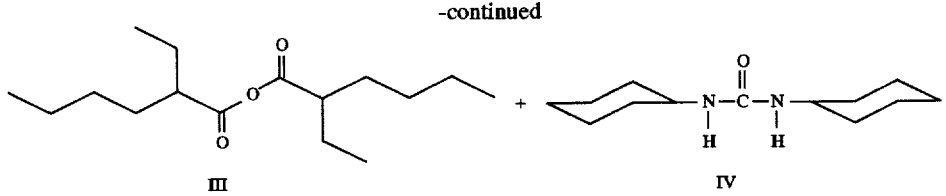

III             IV

The organic acid anhydride can be made from any acid having from 2 to 12 carbon atoms. The anhydride thus has from 4 to 24 carbon atoms. There are two competing considerations in the selection of a suitable acid: the greater the number of carbon atoms, the better the solubility of the subsequent reaction mixture(s), but the higher the carbon content in the film prior to the first decomposition. Consistent with these considerations, an acid in the middle of the range, e.g., 2-ethyl hexanoic acid, is preferably employed.

2. Reaction of Triphenyl Bismuth with Limited 2-ethylhexanoic Acid

To a magnetically stirred mixture of triphenyl bismuth (19.6 g, 0.0445 mol) (V) in toluene (15 g) was added 2-ethylhexanoic acid (12.8 g, 0.089 mol) (I). The reaction was heated at 80° C. for 2 hours and NMR of the solution showed the reaction to be complete.

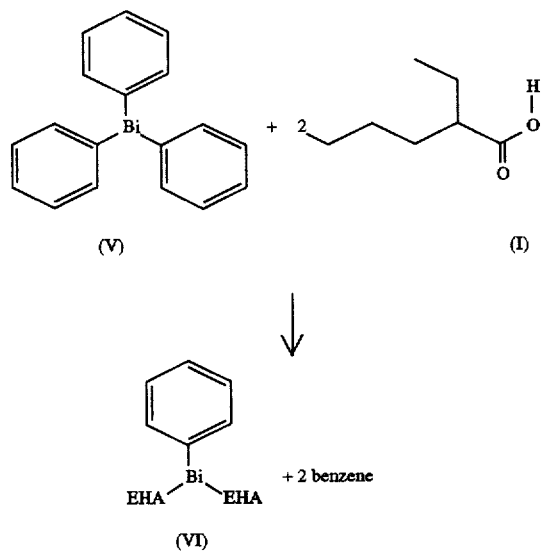

where EHA is the moiety

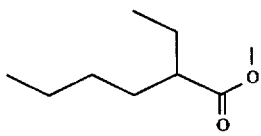

and attachment to the bismuth atom is made through the oxygen bond.

The reason that an alkoxide of bismuth is not employed is simply due to its unavailability commercially; bismuth alkyl and aryl compounds are readily commercially available and hence are preferred. Of these, triphenyl bismuth is most preferred.

The amount of acid employed in this step is less than or equal to a stoichiometric amount relative to the bismuth compound.

3. Reaction of Limited Anhydride with Niobium, Tantalum, and Strontium Metal Alkoxides To compound (VI) formed in step 2 above was added niobium ethoxide (3.18 g, 0.01 mol) (NbOEt$_5$), tantalum ethoxide (13.4 g, 0.033 mol) (TaOEt$_5$), and a solution of strontium-2-methoxy ethoxide, which was formed from the reaction of metallic strontium with 2-methoxyethanol in toluene (20 g, 0.020 mol of strontium; Sr(OCH$_2$CH$_2$OCH$_3$)), and 2-ethylhexanoic acid anhydride (34.0 g, 0.12 mol) (III). The reaction was heated and stirred magnetically at 80° C. overnight. While NMR of the solution showed the reaction to be complete, other examples of this process have shown that the reaction is, in fact, completed in 2 hours or less.

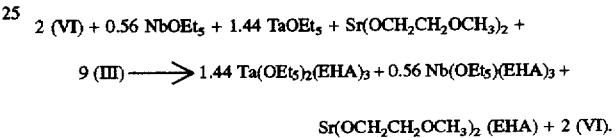

$$9 \text{ (III)} \longrightarrow 1.44 \text{ Ta(OEt}_5)_2(\text{EHA})_3 + 0.56 \text{ Nb(OEt}_5)(\text{EHA})_3 +$$

$$\text{Sr(OCH}_2\text{CH}_2\text{OCH}_3)_2 \text{ (EHA)} + 2 \text{ (VI)}.$$

The alkoxides employed contain from 1 to 5 carbon atoms.

The amount of organic acid anhydride that is added in this step is less than or equal to a stoichiometric amount relative to the metal alkoxide(s). While at least one metal alkoxide may be employed, preferably, a mixture of metal alkoxides is employed.

It will be appreciated that in the preparation of bismuth strontium tantalate-niobate, the tantalum and niobium concentrations may be varied across the entire range from 0 percent to 100% tantalum, thereby enabling a tailoring of electrical properties. This is simply done by adjusting the relative concentrations of the respective alkoxides.

4. Removal of By-product

The 2-ethylhexanoic acid esters formed on reaction of the metal alkoxides with anhydride, as well as the solvent toluene and by-product benzene (from triphenyl bismuth reaction), were removed via vacuum distillation (40° to 100° C., 0.4 torr to give mixed metal alkoxide organic acid materials, shown in the sole FIGURE. The removal of by-product leaves the desired product.

Addition of Water or a Multifunctional Acid or Alcohol (Optional)

To the residue left after distillation in step 5 was added 2-methoxyethanol as solvent (40 g) and water (2.2 g, 0.122 mol). The stirred mixture was heated for 3 hours to effect hydrolysis of the remaining metal alkoxides, and again, NMR was used to determine completion of reaction. This step may be employed or omitted.

5. Final Solvent Exchange and Hydrolysis

Solvent exchange and condensation of the above solution was effected by vacuum distillation of the solvent and hydrolyzed alcohols, followed by addition of xylenes and distillation. A portion of the xylene was distilled off to give a product weighing 220 g, which makes the solution 0.2M in Bi$_{2.18}$Nb$_{0.56}$Ta$_{1.44}$Sr$_{1.00}$. Other solvents may also be employed in the addition step above, such as the larger alkanes, including the $C_7$ to $C_{14}$ alkanes, particularly decane and iso-octane, and esters, such as n-butyl acetate and 2-ethanoic acid ethyl ester. Additional solvents useful in this step are listed in Table A of PCT publication WO 93/12538, supra.

The product that is obtained is a stable mixture of mixed metal organic acid soluble materials having a controlled carbon content. The carbon content is controlled through the selection and stoichiometry of particular organic acids and acid anhydrides employed and hydrolysis of the remaining metal alkoxides.

FABRICATION OF DEVICES

Layered ferroelectric thin film devices are fabricated by first forming the mixture of metal acid organic salts, as described above, then applying the mixture to a preprocessed substrate, and finally heating the mixture to form the layered ferroelectric thin film. Devices are then formed from the thin films. See, also C. A-Paz de Araujo et al, "Fatigue-free ferroelectric capacitors with platinum electrodes", *Nature*, Vol. 374, pp. 627–629 (Apr. 13, 1995).

The mixture of metal acid organic salts is applied to the substrate by a variety of techniques well-known in the processing of semiconductors. A preferred technique is to spin-on the mixture of metal alkoxides onto the substrate.

The spun-on material is then heat treated by placing the wafers on a series of hot plates at increasing temperatures, followed by a rapid thermal annealing and then a furnace firing. The RTA and furnace heating parameters are those commonly employed in the art of forming layered ferroelectric thin film devices; see, e.g., U.S. Pat. No. 5,434,102, supra.

ELECTRICAL PROPERTIES

The solution thus formed using standard spin-on evaporation, rapid thermal annealing (RTA), and furnace firing gave ferroelectric thin films with improved average electrical properties as compared to the prior art. Specifically, the materials provide better lot-to-lot repeatability of the remanant polarization ($2P_r$) and coercive field ($2E_c$) after composition adjustment. This conclusion is illustrated by analysis of the data given in Tables 1 and 2, below. The numbers below the elements Bi, Sr, Ta, and Nb represent the count percentage from selected XRF lines and are related to composition. Table 1 illustrates different lots of thin films made by the Symetrix prior art process and chemistry (referred to herein as "YZ" thin films), showing variability of electrical properties with identical compositions. Table 2 illustrates different lots of YZ thin films made by the Symetrix prior art process and the anhydride process of the present invention, showing variability of electrical properties with identical composition and improvement with the hydrolysis-free anhydride proess of the present invention. Sample 105a was made by the hydrolysis-free anhydride process of the present invention. Sample 124 was made by the anhydride process of the present invention, with 15% hydrolysis. Sample 9–2a was made by the anhydride process of the present invention, with 40% hydrolysis.

TABLE 1

Different Lots of YZ Films Made by Prior Art Process.

| Example | Bi | Sr | Ta | Nb | $2P_r$ | $2E_c$ |
|---|---|---|---|---|---|---|
| | | 1 st Composition | | | | |
| #10475-47 | 44.05 (0.4) | 24.02 (0.2) | 14.71 (0.4) | 17.21 (0.2) | 26.2 | 144 |
| #10475-100 | 43.85 (0.4) | 24.01 (0.2) | 14.76 (0.2) | 17.35 (0.3) | 23.5 | 147 |
| | | 2nd Composition | | | | |
| #7557-92 | 45.94 (0.4) | 21.75 (0.2) | 13.79 (0.2) | 18.49 (0.2) | 21.6 | 145 |
| #7557-17-2 | 45.77 (0.4) | 21.85 (0.5) | 14.32 (0.2) | 18.12 (0.4) | 28.0 | 135 |

TABLE 2

Different Lots of YZ Films Made by Prior Art Process and Anhydride Process of the Present Invention.

| Example | Bi | Sr | Ta | Nb | $2P_r$ | $2E_c$ |
|---|---|---|---|---|---|---|
| #7557-92[1] | 45.94 (0.4) | 21.75 (0.2) | 13.79 (0.2) | 18.49 (0.2) | 21.6 | 145 |
| #7557-17-2[1] | 45.77 (0.4) | 21.85 (0.5) | 14.32 (0.2) | 18.12 (0.4) | 28.0 | 135 |
| #7557-105a[2] | 45.48 (0.3) | 22.15 (0.2) | 14.05 (0.2) | 18.30 (0.2) | 31.5 | 133 |
| #10475-124a[3] | 45.34 (0.2) | 24.09 (0.3) | 14.99 (0.2) | 15.57 (0.2) | 27.5 | 114 |
| #7557-9-2a[4] | 45.77 (0.4) | 23.95 (0.5) | 15.03 (0.2) | 15.26 (0.4) | 23.8 | 115 |

Notes:
[1] Prior art Symetrix process.
[2] Process of present invention, no hydrolysis.
[3] Process of present invention, 15% hydrolysis.
[4] Process of present invention, 40% hydrolysis.

The data in Table 1 represent several lots prepared by the prior art process following composition adjustment; two compositions are illustrated. The data in Table 2 illustrate the variation of properties with identical compositions; two prior art examples and an anhydride example with no hydrolysis (process of the present invention). The data show that the value of $2P_r$, the switchable polarization in $\mu C/cm^2$, is highest for the non-hydrolyzed. The higher the value of $2P_r$, the larger is the memory signal, thus the better the device is for memory applications. Table 2 also shows the value of $2E_c$, which is the coercive field in KV/cm. The samples have nearly the same $2E_c$ value, since they have nearly identical compositions. The lower the value of $2E_c$, the easier for the device to switch. The remaining data in Table 2 show that the properties of the anhydride are variable by changing the hydrolysis. Using the process of the present invention, the anhydride values in Table 2 can be reproduced at will. That is, the electrical properties are consistent for equivalent compositions and hydrolysis. The greater the hydrolysis, the lower the polarization. The composition and the amount of hydrolysis are controllable.

The electrical properties for the anhydride are controllable over the uncontrolled range of the best electrical results of the prior art process. With the prior art process, the hydrolysis is uncontrolled and the electrical properties vary over a larger range.

The present invention provides a much improved method to synthesize MOD solutions, giving better decomposition characteristics, easily changed solvents, and complete control of formation. The materials described here are ferroelectric thin films used, for example, in non-volatile microelectronics memory applications. In addition, different materials made from the process of the present invention (for example, high dielectric constant capacitors and energy storage devices) may be used to greatly improve the performance of focal plane array detectors.

Thus, there has been disclosed an improved method for making in a very controlled manner low carbon content, low decomposition, MOD solutions useful for improved performance of layered ferroelectric thin films. These materials can be produced much faster (and therefore with less cost) than those of the prior art. It will be appreciated by those skilled in this art that various changes and modifications of an obvious nature may be made, and all such changes and modifications are considered to fall within the scope of the present invention, as defined by the appended claims.

What is claimed is:

1. A process for preparing precursor materials for use in fabricating layered, ferroelectric films, comprising:
    (1) providing an organic acid anhydride having from 4 to 24 carbon atoms;
    (2) forming a first reaction mixture of less than or equal to a stoichiometric amount of said organic acid anhydride with more than one metal alkoxide and reacting said first reaction mixture to form a product and by-products;
    (3) removing said by-products to leave said product; and
    (4) adding at least one solvent to said product to provide a solution which comprises a mixture of metal organic acid materials which are soluble in said solvent and having a predetermined carbon content and which forms crack-free films on a substrate.

2. The process of claim 1 further comprising after (1), reacting less than a stoichiometric amount of an organic acid comprising the free acid form with a first bismuth-organic compound to form a second reaction mixture and then, after (2), adding to said second reaction mixture said first reaction mixture to form a third reaction mixture.

3. The process of claim 2 wherein said first bismuth-organic compound comprises an alkyl or aryl complex of bismuth.

4. The process of claim 3 wherein said first bismuth-organic compound consists essentially of triphenyl bismuth.

5. The process of claim 1 wherein said organic acid anhydride consists essentially of 2-ethylhexanoic acid anhydride.

6. The process of claim 1 wherein said metal alkoxide comprises: a metal selected from the group consisting of strontium, calcium, barium, cadmium, lead, titanium, tantalum, hafnium, tungsten, niobium, zirconium, scandium, yttrium, lanthanum, antimony, chromium, and thallium; and an alkoxide having from 1 to 5 carbon atoms.

7. The process of claim 6 employing three metal alkoxides comprising strontium-2-methoxy ethoxide, at least one of niobium ethoxide and tantalum ethoxide and optionally a third metal alkoxide.

8. The process of claim 1 wherein said by-products are removed by vacuum distillation.

9. The process of claim 1 wherein said at least one solvent in (4) is selected from the group consisting of xylenes, $C_7$ to $C_{14}$ alkanes, and esters.

10. The process of claim 1 additionally comprising adding a hydroxy-containing compound to said product resulting from (3), followed by partial or complete hydrolyzation to form said mixture of metal organic acid materials and a hydrolyzed hydroxy-containing compound as a by-product.

11. The process of claim 10 wherein said hydroxy-containing compound is selected from the group consisting of water, a multifunctional acid, and an alcohol.

12. The process of claim 10, further comprising removal of said solvent and said hydrolyzed hydroxyl-containing compound, followed by addition of a second solvent and subsequent distillation to remove said second solvent and provide said mixture of metal organic acid materials.

13. A process for preparing precursor materials for use in fabricating layered, ferroelectric films, comprising:
    (1) providing an organic acid anhydride having from 4 to 24 carbon atoms and an organics acid that is the free acid form of said organic acid anhydride;
    (2) reacting less than or equal to a stoichiometric amount of said organic acid with a bismuth-organic compound to form a first reaction mixture;
    (3) adding to said first reaction mixture a second reaction mixture comprising less than or equal to a stoichiometric amount of said organic acid anhydride and more than one metal alkoxide to form a third reaction mixture and reacting said third reaction mixture to form a product and by-products;
    (4) removing said by-products to leave said product; and
    (5) adding at least one, solvent to said product to provide a solution which comprises a mixture of metal organic acid materials which are soluble in said solvent and having a predetermined carbon content and which forms crack-free films on a substrate.

14. The process of claim 13 wherein said bismuth-organic compound consists essentially of triphenyl bismuth.

15. The process of claim 13 wherein said organic acid anhydride consists essentially of 2-ethylhexanoic acid anhydride.

16. The process of claim 13 employing three metal alkoxides, comprising strontium-2-methoxy ethoxide, at least one of niobium ethoxide and tantalum ethoxide and optionally a third metal alkoxide.

17. The process of claim 13 wherein said at least one solvent in (5) is selected from the group consisting of xylenes, $C_7$ to $C_{14}$ alkanes, and esters.

18. The process of claim 13 additionally comprising adding a hydroxy-containing compound to said product resulting from (4), followed by partial or complete hydrolyzation to form said mixture of metal organic acid materials and a hydrolyzed hydroxy-containing compound as a by-product.

19. The process of claim 18 wherein said hydroxy-containing compound is selected from the group consisting of water, a multifunctional acid, and an alcohol.

20. The process of claim 18, further comprising removal of said solvent and said hydrolyzed hydroxyl-containing compound, followed by addition of a second solvent and subsequent distillation to remove said second solvent and provide said precursor material.

21. A process for fabricating layered ferroelectric films, comprising:

(a) forming a mixture of metal organic acid materials by a process comprising:

(1) providing an organic acid anhydride having from 4 to 24 carbon atoms and an organic acid that is the free acid form of said organic acid anhydride, (2) reacting less than or equal to a stoichiometric amount of said organic acid with a bismuth-organic compound to form a first reaction mixture, (3) adding to said first reaction mixture a second reaction mixture comprising less than or equal to a stoichiometric amount of said organic acid anhydride and more than one metal alkoxide to form a third reaction mixture and reacting said third reaction mixture to form a product and by-products, (4) removing said by-products to leave said product, and (5) adding at least one solvent to said product to provide a solution which comprises a mixture of metal organic acid materials which are soluble in said solvent and having a predetermined carbon content and which forms crack-free films on a substrate;

(b) applying said mixture of metal organic acid materials to a substrate; and (c) heating said mixture of metal organic acid materials to form said layered ferroelectric film.

22. The process of claim 21 wherein said mixture of metal organic acid materials is applied to said substrate by spinning on a solution of said mixture in a solvent.

* * * * *